July 1, 1975 H. E. KENDALL Plant Pat. 3,737
AVOCADO TREE
Filed Feb. 13, 1974
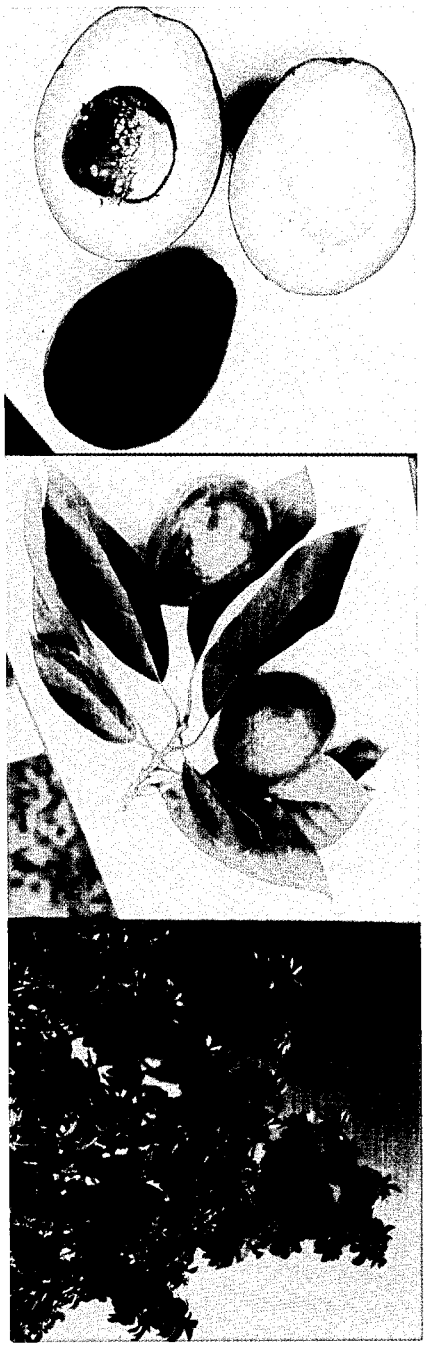

United States Patent

Plant Pat. 3,737

Patented July 1, 1975

3,737

AVOCADO TREE

Harold E. Kendall, P.O. Box 458,
Goulds, Fla. 33170

Filed Feb. 13, 1974, Ser. No. 442,053

Int. Cl. A01h 5/03

U.S. Cl. Plt.—44 1 Claim

This discovery pertains to a new and distinct variety of avocado tree which has many highly desirable characteristics. This new variety was discovered in a cultivated area in my groves in Goulds, Dade County, Fla. As with many avocado varieties, the parentage of this variety is unknown. However, the new variety appears to be a cross of West Indian and Mexican parentage. The variety has been asexually reproduced at Coral Reef Nurseries, operated by me in Goulds, Dade County, Fla., where scions were budded to seedling trees. Other scions were grafted onto trees in groves operated by me in the Goulds-Princeton, Dade County, Fla., area.

This new variety is very desirable since it fills a demand in Florida for a small, good quality avocado in the principal markets of the United States during the late summer and early fall months. It matures during late August, September and early October when there is presently a lack of a small, good quality productive avocado suitable for shipping to the principal markets in the United States. This small to medium size high quality avocado appears to be of better appearance, better eating quality and smaller, more desirable size than other Florida avocados being marketed during the said period.

The accompanying illustrations show a specimen of the fruit cut in half, the individual fruit, the individual fruit and foliage and the original parent tree.

A description of the new variety follows:

SCIENTIFIC NAME

*Persea americana* (The Lisa).

RACE

Hybrid of West Indian and Mexican parentage.

TREE

The original tree is about 18 feet tall, has a slender type of growth with evenly distributed branches and is a vigorous grower. The foliage is of average density and leaves are green to light green. Budded trees are more vigorous and dense and have a darker green foliage than the original tree. The tree is easily propagated by either budding or grafting methods. The subject variety blooms during March and has a "B" type of flower. The original tree has set heavy crops from 1969 to 1972 in spite of it being crowded among older trees. There are usually 2 to 4 fruits per shoot. Fruit is picked beginning in late August through October. The best time for picking appears to be during the month of September.

FRUIT

OUTSIDE: The skin is dark green, shiny and thin. The green color fades slightly by mid-October. The skin is slightly pebbled and free of corky lenticels. Fruit size increases as the harvesting season progresses. Most September fruit is pyriform having a short neck and weighing 10 to 14 ounces. October fruit is usually oval, sometimes having a slanting stylar end, and weighs 15 to 16 ounces.

INSIDE: The flesh is greenish yellow and nearly free of brown fibers. The greenish area around the skin is about ¼ inch thick. Flesh thickness dimension are 1", ½" and 13/16" at the neck, equator and stylar end areas respectively for a 10 ounce fruit, while the respective dimensions for a 16 ounce fruit are 1⅛", ⅝" and 1". Seeds are small to medium in size and tight in the seed cavity. The seed of a 10 ounce fruit is 1¾" wide and 1 15/16" in length, while that of a 16 ounce fruit is 2" wide and 2¼" long.

FRUIT QUALITY

Softening is regular with a absence of hard areas. The fruit retains its external good green color at the soft stage. Flavor is excellent, resembling that of Mexican hybrid seedlings. It is nutty, strong, and sometimes slightly sweet. The texture of the flesh is smooth. It takes an average of 9 days at 70° Farenheit from picking to softening. This will be of special advantage since during this fruit's harvesting season we are shipping avocados all over the United States.

COMPARISON WITH OTHER VARIETIES

| Variety | Season | Size, ounces | Flower, type | Appearance |
|---|---|---|---|---|
| Subject variety (Lisa). | Late August thru September. | 9-14 | B | Small, smooth, thin skin, round to oval. |
| Miguel (unpatented). | -----do--------- | 20-48 | B | Large, shiny, dark, slightly leathery green, with cleft. |
| Meya (Plant Pat. No. 3116). | Janurary thru March. | 10-14 | B | Oblongate, small, dark green pebbled with prominate lenticels. |
| Zio (Plant Pat. No. 3117). | December to February. | 9-13 | B | Small, rough, pebbled dark green oblong. |

Having thus described my discovery, I claim:

1. A new and distinct variety of avocado tree, substantially as shown and described.

No references cited.

ROBERT E. BAGWILL, Primary Examiner.